(12) United States Patent
Kim et al.

(10) Patent No.: US 11,007,314 B2
(45) Date of Patent: May 18, 2021

(54) APPARATUS FOR PREVENTING BACKFLOW

(71) Applicant: ENGAIN, Seongnam-si (KR)

(72) Inventors: Dong Chul Kim, Suwon-si (KR); Young Gook Koh, Seongnam-si (KR)

(73) Assignee: ENGAIN, Seongnam-si (KR)

( * ) Notice: Subject to any disclaimer, the term of this patent is extended or adjusted under 35 U.S.C. 154(b) by 0 days.

(21) Appl. No.: 16/998,701

(22) Filed: Aug. 20, 2020

(65) Prior Publication Data

US 2021/0052806 A1    Feb. 25, 2021

(30) Foreign Application Priority Data

Aug. 23, 2019   (KR) .................. 10-2019-0103400

(51) Int. Cl.
*A61M 5/14*   (2006.01)
(52) U.S. Cl.
CPC ....... *A61M 5/14* (2013.01); *A61M 2005/1406* (2013.01)
(58) Field of Classification Search
CPC ............... E03C 1/106; Y10T 137/3331; Y10T 137/3149; Y10T 137/7922; Y10T 137/88054; F16K 11/105; F16K 15/066; F16K 17/04; F16K 17/048; A61M 5/14; A61M 2005/1406
See application file for complete search history.

(56) References Cited

U.S. PATENT DOCUMENTS 8,042,565 B2 * 10/2011 Ball ................ E03C 1/106
                                              137/218

2004/0134537 A1   7/2004 Noll
2019/0093775 A1   3/2019 Feith et al.

FOREIGN PATENT DOCUMENTS

| JP | 04013155 U | 2/1992 |
|----|------------|--------|
| JP | 4339682 B2 | 10/2009 |
| KR | 20-1997-0056956 U | 11/1997 |
| KR | 10-2003-0014522 A | 2/2003 |
| KR | 10-1082981 | 11/2011 |

(Continued)

OTHER PUBLICATIONS

Office Action issued in KR 10-2019-0103400; mailed by the Korean Intellectual Property Office dated Mar. 3, 2020.

(Continued)

*Primary Examiner* — Brandy S Lee
(74) *Attorney, Agent, or Firm* — Studebaker & Brackett PC

(57) ABSTRACT

An apparatus for preventing backflow includes a body forming an accommodating portion which forms a transport passage of a fluid inward, wherein the accommodating portion comprises a double backflow prevention chamber to prevent backflow of the fluid, and a double backflow prevention member provided in the accommodating portion and stepwise implementing opening and closing of the double backflow prevention chamber, In particular, the accommodating portion includes an inflow chamber provided at an upper portion of the body and into which the fluid flows; a discharge chamber through which the fluid is discharged to a lower portion of the inflow chamber; and the double backflow prevention chambers respectively provided at the lower portion of the inflow chamber and the upper portion of the discharge chamber.

13 Claims, 15 Drawing Sheets

(56) References Cited

FOREIGN PATENT DOCUMENTS

KR    10-2019-0073683 A    6/2019

OTHER PUBLICATIONS

Office Action issued in KR 10-2019-0103400; mailed by the Korean Intellectual Property Office dated Oct. 31, 2019.
The extended European search report issued by the European Patent Office dated Oct. 28, 2020, which corresponds to European Patent Application No. 20192042.8-1122 and is related to U.S. Appl. No. 16/998,701.

* cited by examiner

APPARATUS FOR PREVENTING BACKFLOW

CROSS-REFERENCE TO RELATED APPLICATION

This application claims priority from Korean Patent Application No. 10-2019-0103400 filed on Aug. 23, 2019 in the Korean Intellectual Property Office, and all the benefits accruing therefrom under 35 U.S.C. 119, the contents of which in their entirety are herein incorporated by reference.

BACKGROUND

1. Technical Field

The present invention relates to an apparatus for preventing backflow, and more specifically, to an apparatus for preventing backflow that can prevent blood from flowing backward in the course of supplying while supplying a liquid medicine or fluid to a body smoothly.

2. Description of the Related Art

Generally, a fluid set refers to a medical product used for injecting a fluid or a liquid medicine into a human body for medical purposes. The fluid set is used for intravenous injection.

The general form of the fluid set consists of a chamber coupled to a pharmaceutical container, a regulator, a hub coupled to an intravenous catheter, and a tube to connect the chamber to the hub. In addition, the infusion of the fluid by the fluid set is performed by a method of inserting the intravenous catheter into a blood vessel and connecting the hub of the intravenous catheter with the fluid set.

Conventional intravenous catheter uses a flexible material for the protection of blood vessels, and it constitutes a unit with a metal guide needle and is used to facilitate vascular access. When the guide needle and the intravenous catheter are configured as a unit, the guide needle penetrates a skin and serves to guide the vascular entry of the intravenous catheter, and then is separated from the intravenous catheter and discarded. The intravenous catheter acts to supply the fluid into the blood vessel by connecting the fluid set to the hub while entering the blood vessel.

The regulator may implement a function of adjusting the dosage of the fluid when the fluid of the fluid set is supplied through the hub while the intravenous catheter is entered into a blood vessel of a patient. The regulator may be provided in the intravenous catheter or may be provided in a predetermined position of the hub.

In conventional injection needles for fluid injection, when a position of the fluid injector is significantly lower than that of the patient's body during injection, or when a position of the patient's heart is higher than that of the fluid injector due to the patient's movement, the pressure in blood vessels increases. Therefore, the pressure of the blood vessel is relatively higher than the pressure of the fluid injected into the blood vessel. As a result, a problem may arise in which the fluid is pushed out and blood flows out of the patient's body through the intravenous catheter.

The backwardly flowed blood mixes with the fluid, and platelet necrosis begins immediately. The necrotic platelets may eventually block the intravenous catheter, which may cause difficulty in injecting the fluid.

Therefore, there is a need for an apparatus for preventing backflow that can prevent blood from flowing backward in the course of supplying while supplying a liquid medicine or fluid to a body smoothly.

SUMMARY

Aspects of the present invention provide an apparatus for preventing backflow, in which the apparatus is provided in an intravenous catheters or a hub, and can stably carry a forward movement of a fluid, while blocking the movement in a reverse direction.

However, aspects of the present invention are not restricted to those set forth herein. The above and other aspects of the present invention will become more apparent to one of ordinary skill in the art to which the present invention pertains by referencing the detailed description of the present invention given below.

According to an aspect of an exemplary embodiment, there is provided an apparatus for preventing backflow, comprising: a body forming an accommodating portion which forms a transport passage of a fluid inward, wherein the accommodating portion comprises a double backflow prevention chamber to prevent backflow of the fluid; and a double backflow prevention member provided in the accommodating portion and stepwise implementing opening and closing of the double backflow prevention chamber,
wherein the accommodating portion comprises:
an inflow chamber provided at an upper portion of the body and into which the fluid flows; a discharge chamber through which the fluid is discharged to a lower portion of the inflow chamber; and the double backflow prevention chambers respectively provided at the lower portion of the inflow chamber and the upper portion of the discharge chamber, the double backflow prevention chamber comprising a first chamber provided below the inflow chamber and a second chamber provided below the discharge chamber and connected to the first chamber, and
wherein the double backflow prevention member comprises: a first prevention member provided between the inflow chamber and the first chamber to open and close between the inflow chamber and the first chamber; a second prevention member coupled to the first prevention member and provided between the first chamber and the second chamber to open and close between the first chamber and the second chamber; and an elastic member provided between the second prevention member and a bottom surface of the first chamber to elastically support and move the first prevention member and the second prevention member.

A first opening connected to the inflow chamber and opened or closed through the double backflow prevention member may be formed in an upper portion of the first chamber, and wherein a second opening connected to the first chamber and opened or closed through the double backflow prevention member may be formed in an upper portion of the second chamber.

A third opening connected to the second opening may be formed in a lower portion of the first chamber, and wherein a connection flow path connecting the third opening and the second opening may be formed between the first chamber and the second chamber.

The first prevention member may be provided to open and close the first opening by moving an up and down direction by an inflow pressure of the fluid between the inflow chamber and the first chamber, and wherein the second prevention member may be provided to open and close the second opening according to an upward and downward movement of the first prevention member between the first chamber and the second chamber.

The first prevention member comprises: a first body formed in a conical shape and forming an accommodating space accommodated in one end of the second prevention member inward; and a pressing member protruding in a lateral direction in a circumference of a lower surface of the body, the pressing member engaging with an upper surface of the first chamber and opening and closing the first opening as it moves.

A guide protrusion for guiding a flow of the fluid in a conical shape may be further formed on an upper portion of the first body to be stepped with the first body.

A flow rate portion that is recessed inward to accelerate a flow rate of the fluid may be formed on a circumferential surface of the inflow chamber in which the first body is positioned.

The upper surface of the first chamber may form an inner inclined surface lowering toward a direction of the first opening, and one surface of the pressing member may form a pressing inclined surface corresponding to the inner inclined surface, thereby causing the pressing inclined surface to face the inner inclined surface to close the first opening.

An inlet surface may be formed on the other surface of the pressing member to flow inwardly corresponding to the one surface of the second prevention member.

A coupling hole in which one end of the second prevention member may be inserted into the accommodating space and may be movably formed is formed in the inlet surface.

The second prevention member comprises: a second body provided between the bottom surface of the first chamber and the inlet surface; a head provided to be connected to the upper portion of the first body through a first connecting protrusion, the head being accommodated in the accommodating space and coupled so as to prevent from being separated from the first body; and a sealing portion provided to be connected to a lower portion of the second body through a second connecting protrusion and disposed inside the second chamber, the sealing portion opening or closing the second opening according to a raising and lowering movement of the second prevention member.

One surface and the other surface of the second body may form convex surfaces convex in the up and down direction, respectively, with respect to the first connecting protrusion and the second connecting protrusion.

The convex surface of the one surface of the second body may be in contact with or released from the inlet surface according to a raising and lowering movement of the first prevention member.

A protrusion protruding upward may be provided around a periphery of the third opening in the bottom surface of the first chamber, and the elastic member may be disposed between the inlet surface in a circumferential surface of the second body and the bottom surface of the first chamber toward an inside of the projection, thereby providing an elastic force to the first prevention member.

The sealing portion may be formed in a convex dish shape.

In accordance with an apparatus for preventing backflow according to an embodiment of the present invention, when a fluid enters a body, the fluid may flow into the body at a constant speed by allowing the fluid to be opened stepwise through the movement of a backflow prevention member.

In addition, in accordance with an apparatus for preventing backflow according to an embodiment of the present invention, when a situation in which blood flows in a reverse direction occurs because the pressure higher than the pressure of the fluid is generated in the reverse direction to a direction of the fluid inflow in flowing the fluid, it is possible to prevent the blood from flowing backward in the reverse direction by being closed stepwise through the movement of the backflow prevention member.

The effects of the present invention are not limited to the above-described effects and other effects which are not described herein will become apparent to those skilled in the art from the following description.

BRIEF DESCRIPTION OF THE DRAWINGS

The above and other aspects and features of the present invention will become more apparent by describing in detail exemplary embodiments thereof with reference to the attached drawings, in which.

DETAILED DESCRIPTION OF THE EMBODIMENTS

Figure 1:
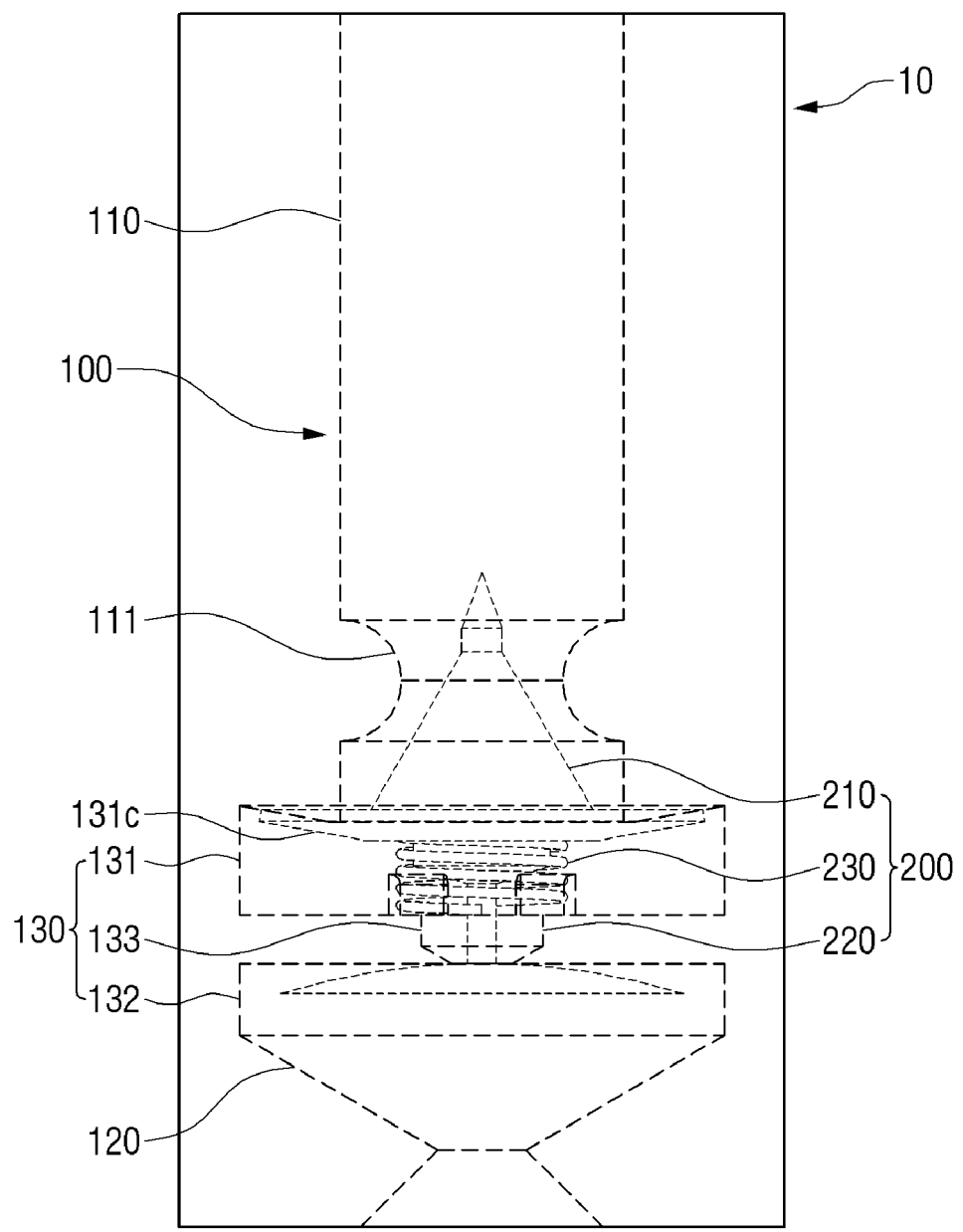
FIG. 1 is a view schematically showing a combined state of an apparatus for preventing backflow according to an embodiment of the present invention.

Advantages and features of the disclosure and methods to achieve them will become apparent from the descriptions of exemplary embodiments herein below with reference to the accompanying drawings. However, the inventive concept is not limited to exemplary embodiments disclosed herein but may be implemented in various ways. The exemplary embodiments are provided for making the disclosure of the inventive concept thorough and for fully conveying the scope of the inventive concept to those skilled in the art. It is to be noted that the scope of the disclosure is defined only by the claims. Like reference numerals denote like elements throughout the descriptions.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

Terms used herein are for illustrating the embodiments rather than limiting the present disclosure. As used herein, the singular forms are intended to include plural forms as well, unless the context clearly indicates otherwise. Throughout this specification, the word "comprise" and variations such as "comprises" or "comprising," will be understood to imply the inclusion of stated elements but not the exclusion of any other elements.

Hereinafter, exemplary embodiments of the present disclosure will be described in detail with reference to the accompanying drawings.

Figure 2:
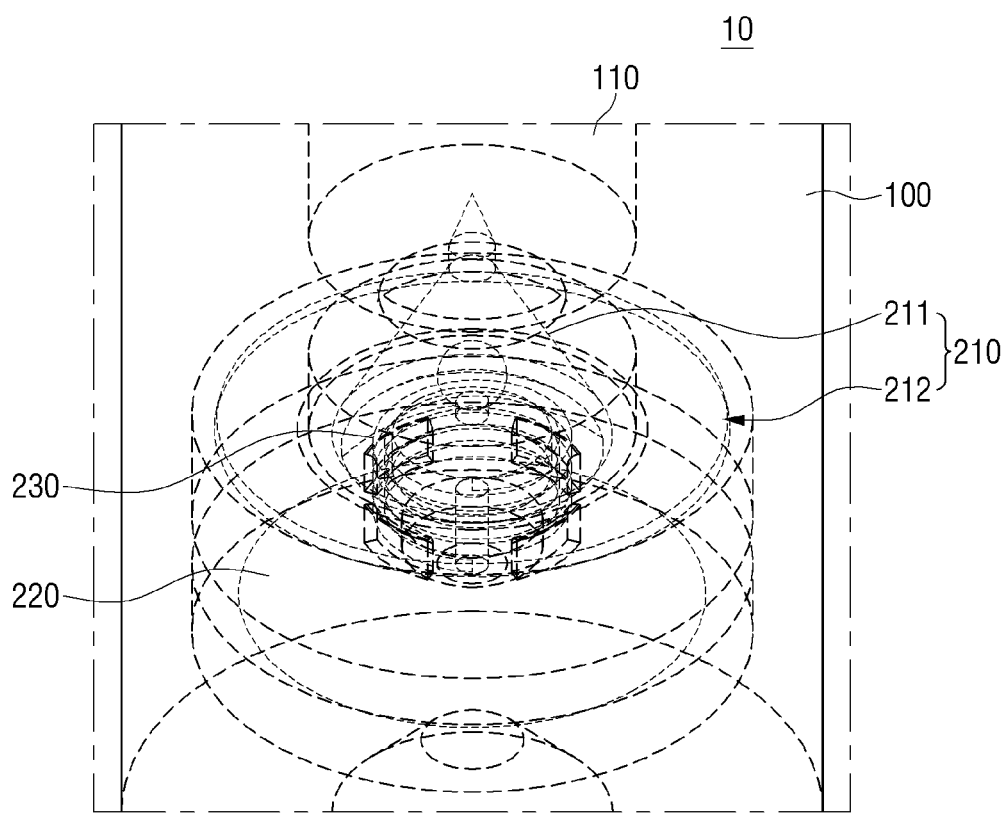
FIG. 2 is a schematic partial perspective view showing the combined state of the apparatus for preventing backflow according to the embodiment of the present invention.

FIG. 1 is a view schematically showing a combined state of an apparatus 1 for preventing backflow according to an embodiment of the present invention. FIG. 2 is a schematic partial perspective view showing the combined state of the apparatus 1 for preventing backflow according to the embodiment of the present invention.

Referring to FIGS. 1 and 2, the apparatus 1 for preventing backflow according to the embodiment of the present invention may include a body 10 and a double backflow prevention member 200.

According to the embodiment, an accommodating portion 100 is formed inside the body 10 to form a transport passage for a fluid, in which a double backflow prevention chamber 130 capable of preventing backflow of the fluid may be formed in the accommodating portion 100.

The double backflow prevention member 200 may be provided in the accommodating portion 100, specifically, the double backflow prevention chamber 130, and may be provided in the double backflow prevention chamber 130 to implement opening and closing step by step with each other.

Figure 3:
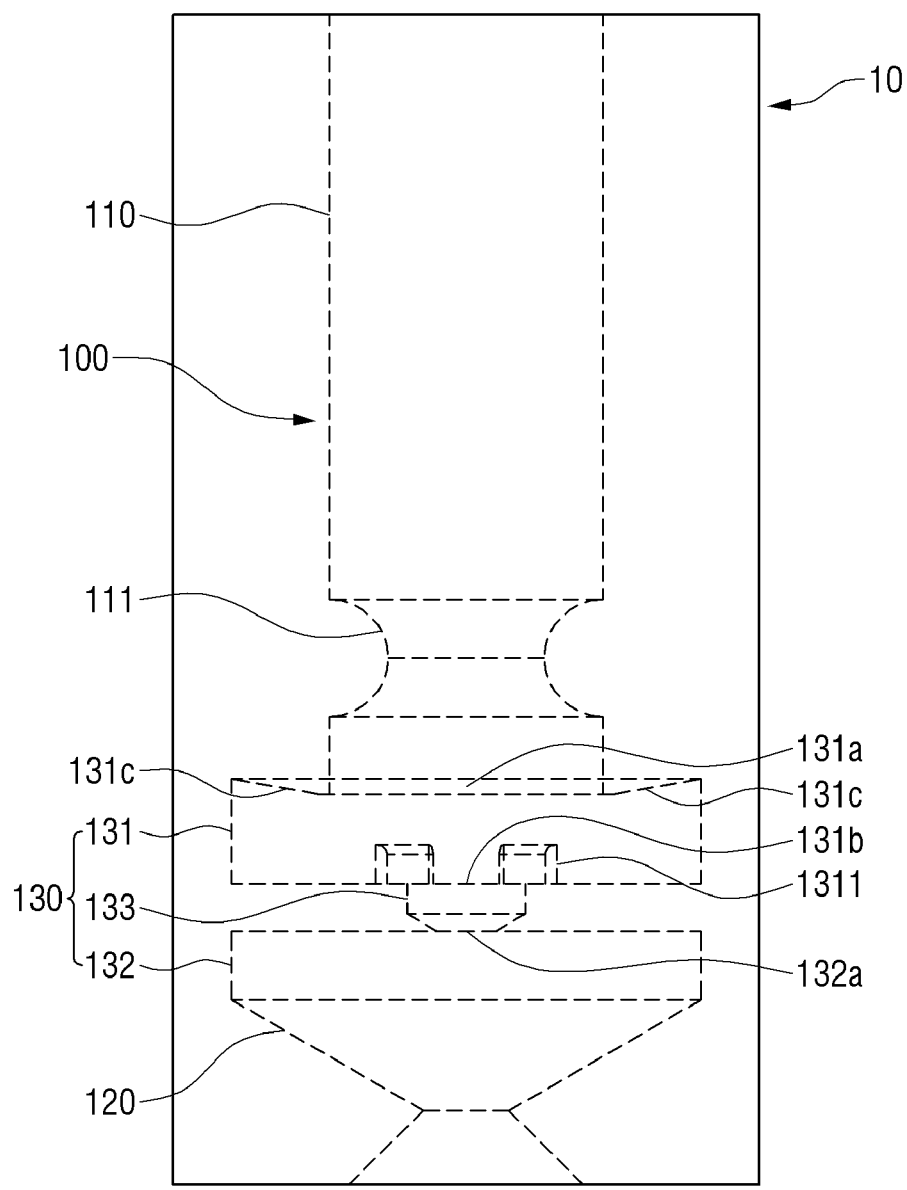
FIG. 3 is a cross-sectional view of a body in the apparatus for preventing backflow according to the embodiment of the present invention.
Figure 4:
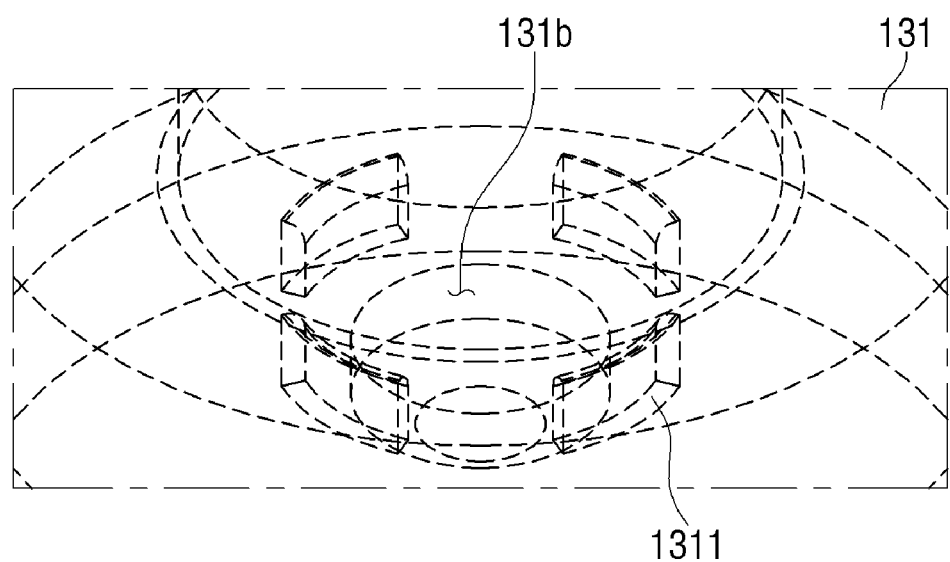
FIG. 4 is a schematic perspective view of a first chamber formed inside the body in the apparatus for preventing backflow according to the embodiment of the present invention.

FIG. 3 is a cross-sectional view of the body 10 in the apparatus 1 for preventing backflow according to the embodiment of the present invention. FIG. 4 is a schematic perspective view of a first chamber 131 formed inside the body 10 in the apparatus 1 for preventing backflow according to the embodiment of the present invention.

Referring to FIGS. 3 and 4, the accommodating portion 100 of the present invention is provided inside the body 10. As a configuration that allows the fluid to move in a body direction, it may include an inflow chamber 110, a discharge chamber 120, and the double backflow prevention chamber 130.

The inflow chamber 110 is provided in an upper portion of the body 10 and is a chamber through which the fluid flows. The fluid flowed into the inflow chamber 110 by the opening or closing by the first prevention member 210 of the backflow prevention member described below may be flown or flow may be restricted.

The inflow chamber 110 is formed in a hollow cylinder shape. A flow rate portion 111 may be formed at a lower end side of the inflow chamber 110. The flow rate portion 111 is narrowed so as to increase pressure by accelerating a flow rate of the fluid to a position of the first prevention member 210 to be described later. For example, the flow rate portion 111 may be provided to be formed to be recessed inward from an outer surface of the inflow chamber 110.

An lower end of the inflow chamber 110 may be connected to the double backflow prevention chamber 130, which will be described later, specifically the first chamber 131. A width of the inflow chamber 110 may be formed smaller than a width of the double backflow prevention chamber 130.

The discharge chamber 120 is provided below the accommodating portion 100, and is provided below the double backflow prevention chamber 130. The fluid flowed into the double backflow prevention chamber 130 may be discharged through the discharge chamber 120. The discharge chamber 120 may be provided in a shape that narrows toward a bottom.

The double backflow prevention chamber 130 may be provided below the inflow chamber 110 and above the discharge chamber 120, respectively. The double backflow prevention chamber 130 may include the first chamber 131, a second chamber 132, and a connection flow path 133.

The first chamber 131 is provided below the inflow chamber 110 and is directly connected to the lower portion of the inflow chamber 110. Here, the first chamber 131 may be provided larger than an outer circumference of the inflow chamber 110. A first opening 131*a* connected to the inflow chamber 110 and opened or closed through the double backflow prevention member 200 may be formed at an upper portion of the first chamber 131. A third opening 131*b* connected to a connection flow path 133 connected to the second chamber 132 may be formed at a lower portion of the first chamber 131.

In addition, an upper surface of the first chamber 131 may be provided to form an inner inclined surface 131*c* lowering toward the first opening 131*a*.

A protrusion 1311 protruding upward may be provided around a periphery of the third opening in a bottom surface of the first chamber 131. The protrusion 1311 may support movement when moving up and down of a second prevention member 220 described later while fixing movement of one end of an elastic member 230 to be described later.

The second chamber 132 may have the same width as the first chamber 131. The second chamber 132 is provided below the first chamber 131, and is provided at a predetermined distance. The second chamber 132 may be provided to be directly connected to the discharge chamber 120 above the discharge chamber 120. A second opening 132*a* connected to the first chamber 131 and opened or closed through the double backflow prevention member 200 may be formed at an upper portion of the second chamber 132.

The connection flow path 133 is provided between the first chamber 131 and the second chamber 132, and may have a structure that connects the third opening 131*b* and the second opening 132*a*.

Figure 5:
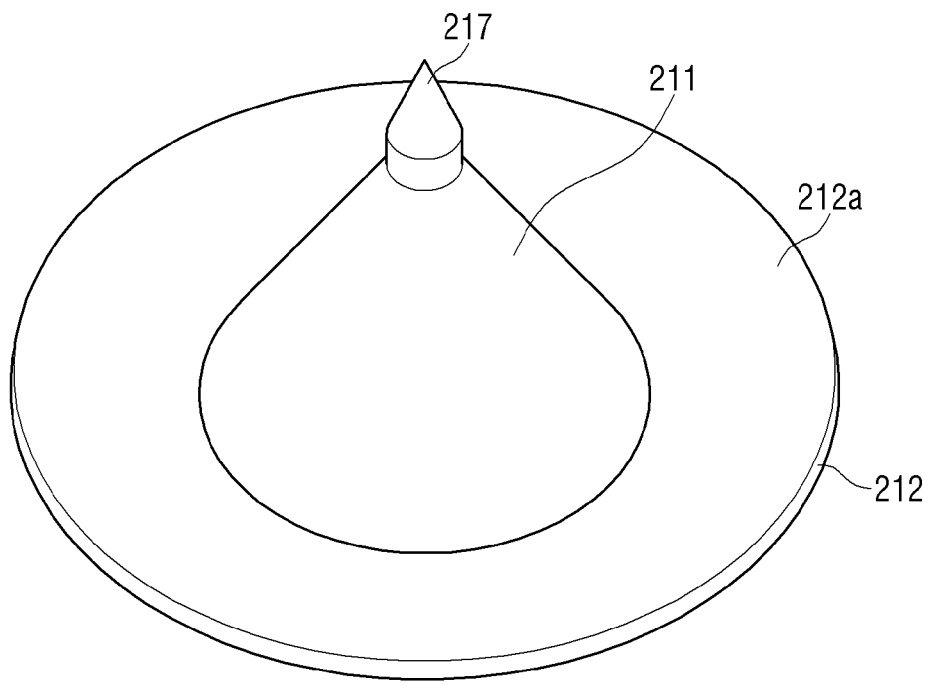
FIG. 5 is a perspective view in one direction schematically showing a first prevention member of a backflow prevention member in the apparatus for preventing backflow according to the embodiment of the present invention.
Figure 6:
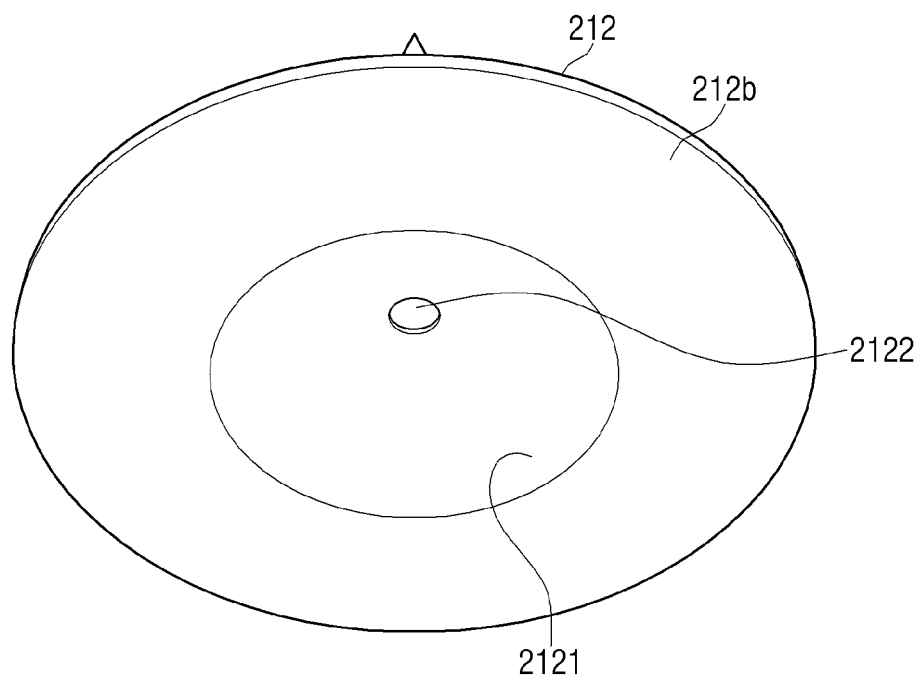
FIG. 6 is a perspective view in another direction schematically showing the first prevention member of the backflow prevention member in the apparatus for preventing backflow according to the embodiment of the present invention.
Figure 7:
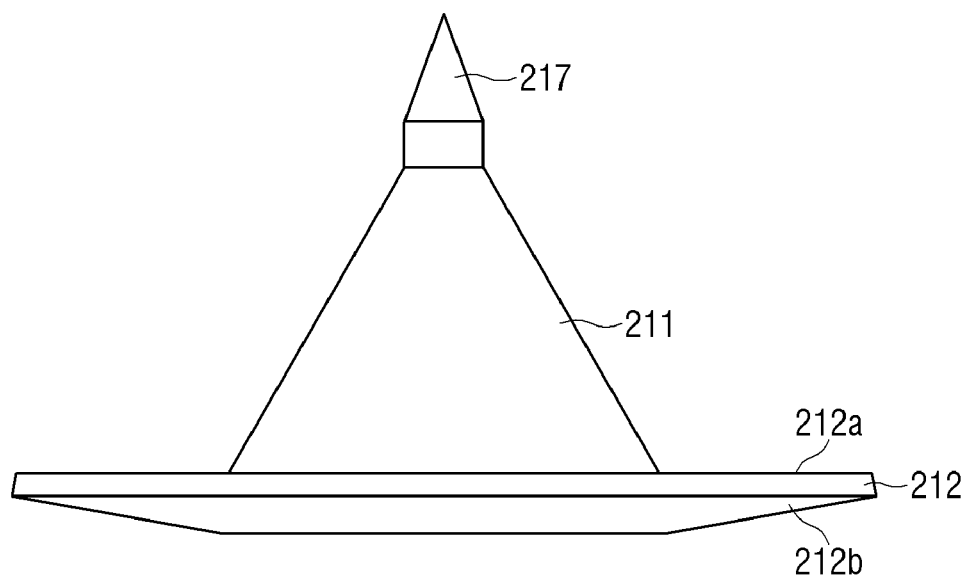
FIG. 7 is a front view schematically showing the first prevention member of the backflow prevention member in the apparatus for preventing backflow according to the embodiment of the present invention.

FIG. 5 is a perspective view in one direction schematically showing the first prevention member 210 of the backflow prevention member in the apparatus 1 for preventing backflow according to the embodiment of the present invention. FIG. 6 is a perspective view in another direction schematically showing the first prevention member 210 of the backflow prevention member in the apparatus 1 for preventing backflow according to the embodiment of the present invention. FIG. 7 is a front view schematically showing the first prevention member 210 of the backflow prevention member in the apparatus 1 for preventing backflow according to the embodiment of the present invention.

Referring to FIGS. 5 to 7, the double backflow prevention member 200 according to the embodiment of the present invention may be positioned at the first chamber 131 and the second chamber 132 at an end of the inflow chamber 110, and may open and close the first opening 131*a* and the second opening 132*a* stepwise. Therefore, the fluid flowing into the inflow chamber 110 flows into the discharge chamber 120, and blood or the like flowing into the discharge chamber 120 is blocked from flowing into the inflow chamber 110.

Specifically, the double backflow prevention member 200 may include the first prevention member 210, the second prevention member 220, and the elastic member 230.

The first prevention member 210 may be provided between the end of the inflow chamber 110 and the first chamber 131. The first prevention member 210 has a structure in which the first opening 131*a* is opened while being pushed downward by the inflow pressure of the fluid provided from the top. Conversely, when pressure is generated, the first prevention member 210 has a structure in which the second opening 132*a* is closed while being pushed upward.

The first prevention member 210 according to the embodiment of the present invention may have a cone shape, and may include a first body 211 and a pressing member 212.

The first body 211 is formed in a conical shape. An accommodating space accommodated at an end of the second prevention member 220 may be formed inside the first body 211. A guide protrusion 217 for guiding the flow of the fluid in a conical shape to be stepped with the first body 211 may be further formed on an upper portion of the first body 211.

The guide protrusion 217 is positioned at an upper portion of the flow rate portion 111 of the inflow chamber 110. Therefore, a hydraulic pressure may be increased as the fluid flows between the flow rate portion 111 and the guide protrusion 217.

The pressing member 212 may be formed to protrude in a lateral direction from a circumference of a lower surface of the first body 211. In addition, one surface of the pressing member 212 may form a pressing inclined surface 212*a* in close contact with the inner inclined surface 131*c*.

The one surface of the pressing member 212, specifically, the pressing inclined surface 212*a* is in close contact with the inner inclined surface 131*c* to an upper surface of the first chamber 131 to close the first opening 131*a*. In this state, when the hydraulic pressure of the fluid is generated, the pressing member 212 is pressed and lowered due to the hydraulic pressure of the fluid. The pressing inclined surface 212*a* of the pressing member 212 is spaced apart from the inner inclined surface 131*c*, and opens the first opening 131*a*.

In addition, an inlet surface 2121 may be formed on the other surface 212*b* of the pressing member 212 to flow inwardly corresponding to the one surface of the second prevention member 220. The inlet surface 2121 may be formed in a concave spherical shape, and is configured to be in contact with or released from the second prevention member 220 described later. A coupling hole 2122 may be formed in the inlet surface 2121. The coupling hole 2122 is a hole in which a first connecting protrusion 225 is movably provided in a state where the one end of the second prevention member 220 is inserted into the accommodating space.

Figure 8:
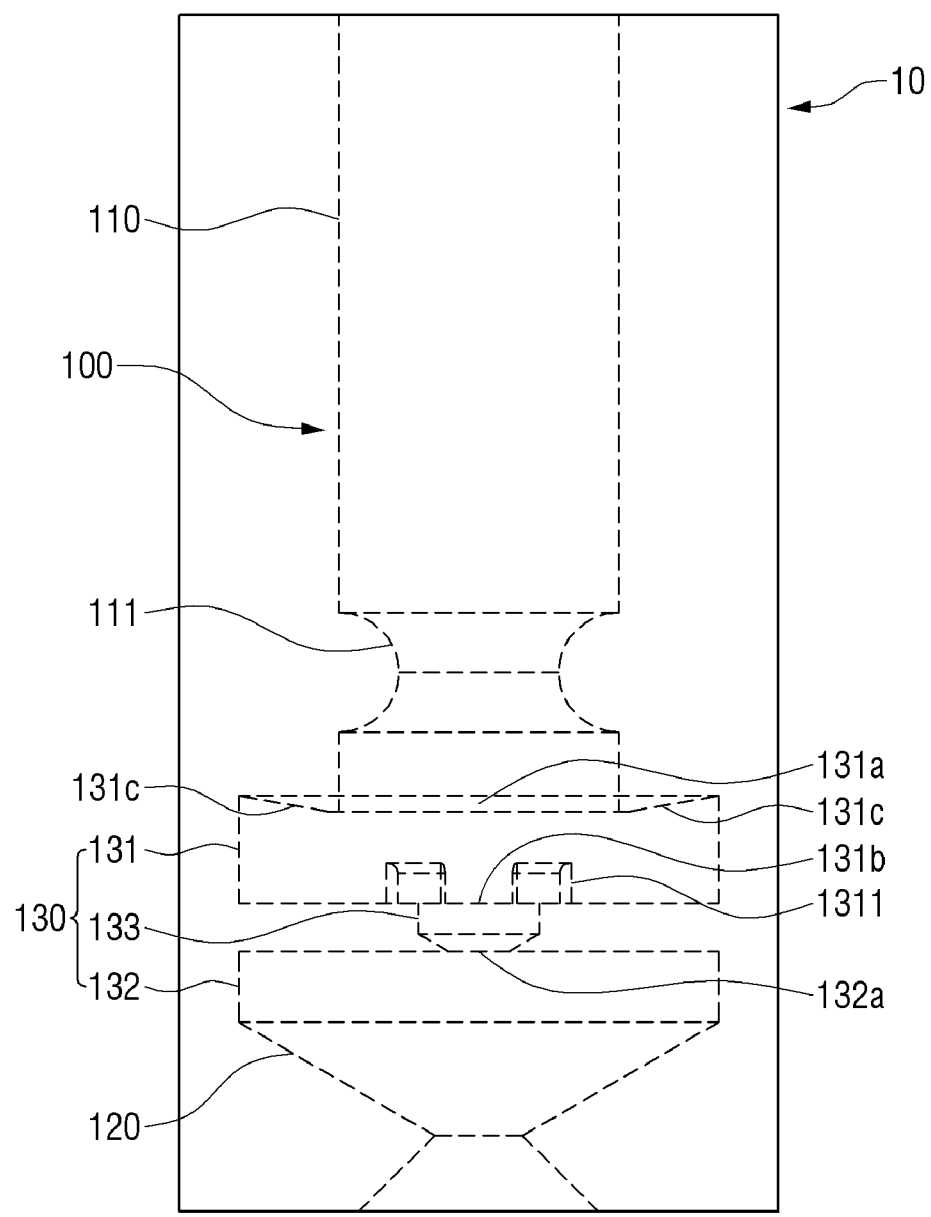
FIG. 8 is a perspective view in one direction schematically showing a second prevention member of the backflow prevention member in the apparatus for preventing backflow according to the embodiment of the present invention.
Figure 9:
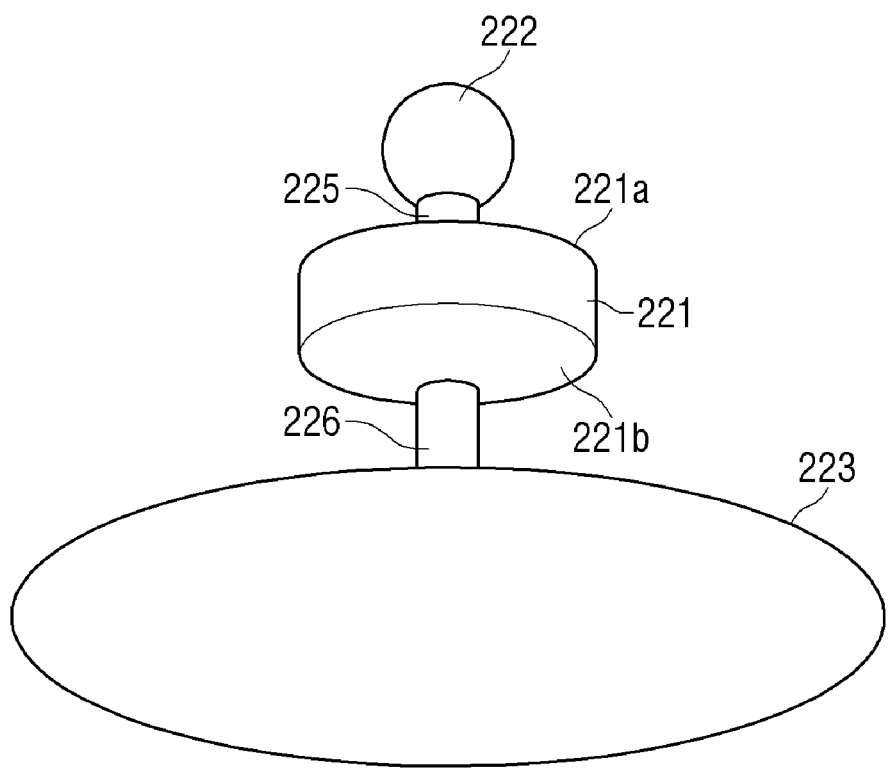
FIG. 9 is a perspective view in another direction schematically showing the second prevention member of the backflow prevention member in the apparatus for preventing backflow according to the embodiment of the present invention.
Figure 10:
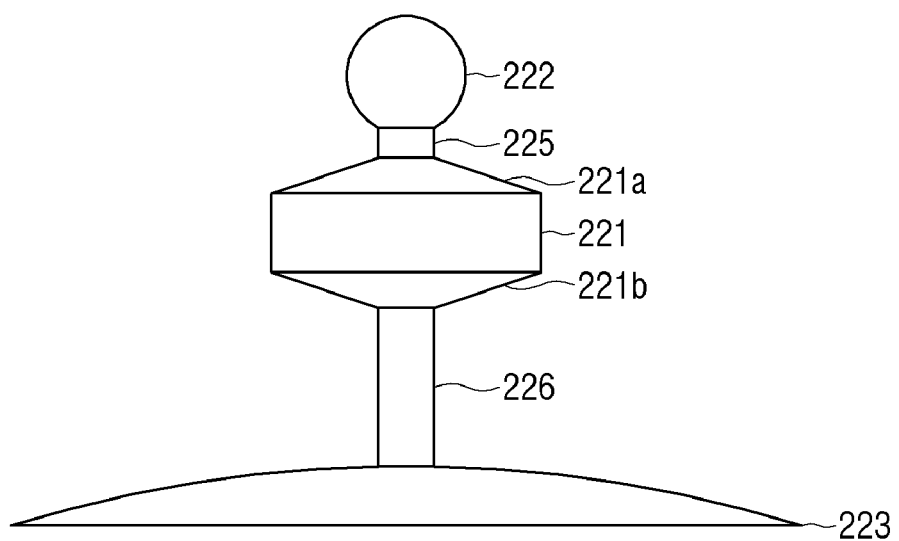
FIG. 10 is a front view schematically showing the second prevention member of the backflow prevention member in the apparatus for preventing backflow according to the embodiment of the present invention.

FIG. 8 is a perspective view in one direction schematically showing the second prevention member 220 of the backflow prevention member in the apparatus 1 for preventing backflow according to the embodiment of the present invention. FIG. 9 is a perspective view in another direction schematically showing the second prevention member 220 of the backflow prevention member in the apparatus 1 for preventing backflow according to the embodiment of the present invention. FIG. 10 is a front view schematically showing the second prevention member 220 of the backflow prevention member in the apparatus 1 for preventing backflow according to the embodiment of the present invention.

Referring to FIGS. 8 to 10, the double backflow prevention member 200 according to the embodiment of the present invention includes the second prevention member together with the first prevention member 210. When the first opening 131*a* is opened and closed by the first prevention member 210, the second opening 132*a* may be opened and closed by the second prevention member 220.

Specifically, the second prevention member 220 is coupled to the first prevention member 210, and may be provided to connected between the first chamber 131 and the second chamber 132. The second prevention member 220 may be provided to be moved in the up and down direction in response to the driving of the first prevention member 210. The second prevention member 220 may be provided to open and close the second opening 132*a* while being moved according to the upward and downward movement of the first prevention member 210.

The second prevention member 220 may include a second body 221, a head 222 and a sealing portion 223, and a first connecting protrusion 225 and a second connecting protrusion 226.

The second body 221 may be positioned between the other surface of the pressing member 212, specifically, the inlet surface 2121 and the bottom surface of the first chamber 131. The second body 221 may contact the inlet surface 2121 or the bottom surface of the first chamber 131 according to the upward and downward movement.

The head 222 and the sealing portion 223 are positioned at upper and lower portions of the second body 221, respectively. Here, the first connecting protrusion 225 may be formed to connect the second body 221 and the head 222, and the second connecting protrusion 226 may be formed to connect the second body 221 and the sealing portion 223.

Convex surfaces 221*a* and 221*b* may be formed on one surface and the other surface of the second body 221, respectively.

The convex surface (hereinafter, referred to as an upper convex surface 221*a*) formed on the one surface of the second body 221 may be provided convexly or inclined to lower around the first connecting protrusion 225. The upper convex surface 221*a* may be provided to be in contact with or released from the contact surface 2121 of the pressing member 212 according to the movement of the first prevention member 210 or the second prevention member 220.

The convex surface (hereinafter, referred to as a lower convex surface 221b) formed on the other surface of the second body 221 may be convex or inclined to lower around the second connecting protrusion 226. The lower convex surface 221b may be provided to be in contact with or released from the bottom surface of the first chamber 131 according to the movement of the second prevention member 220.

The head 222 may be positioned above the first body 211, and the head 222 may be provided to be connected to the first body 211 through the first connecting projection 225. The head 222 may be coupled to be accommodated in the accommodating space so as to prevent from being separated from the first body 211. For example, when the second prevention member 220 is moved in the up and down direction, the head 222 may be lowered while seated in the accommodating space. When the head 222 is lowered a predetermined length due to the lowering of the head 222, it is caught in the coupling hole 2122. The head 222 may be formed in a round spherical shape.

The sealing portion 223 may be positioned under the second body 221, and the sealing portion 223 may be provided to be connected to a lower portion of the second body 221 through the second connecting protrusion 226. The second connecting protrusion 226 is provided in the connection flow path 133 between the first chamber 131 and the second chamber 132, so that the second body 221 may be positioned inside the first chamber 131, and the sealing portion 223 may be positioned inside the second chamber 132. As described above, the sealing portion 223 may be disposed inside the second chamber 132, and be provided in close contact with an upper surface of the second chamber 132, so that it opens or closes the second opening 132a according to the lifting and lowering movement of the second prevention member 220.

The sealing portion 223 may be formed in a dish shape that is convexly formed downwardly around the second connecting protrusion 226.

Figure 11:
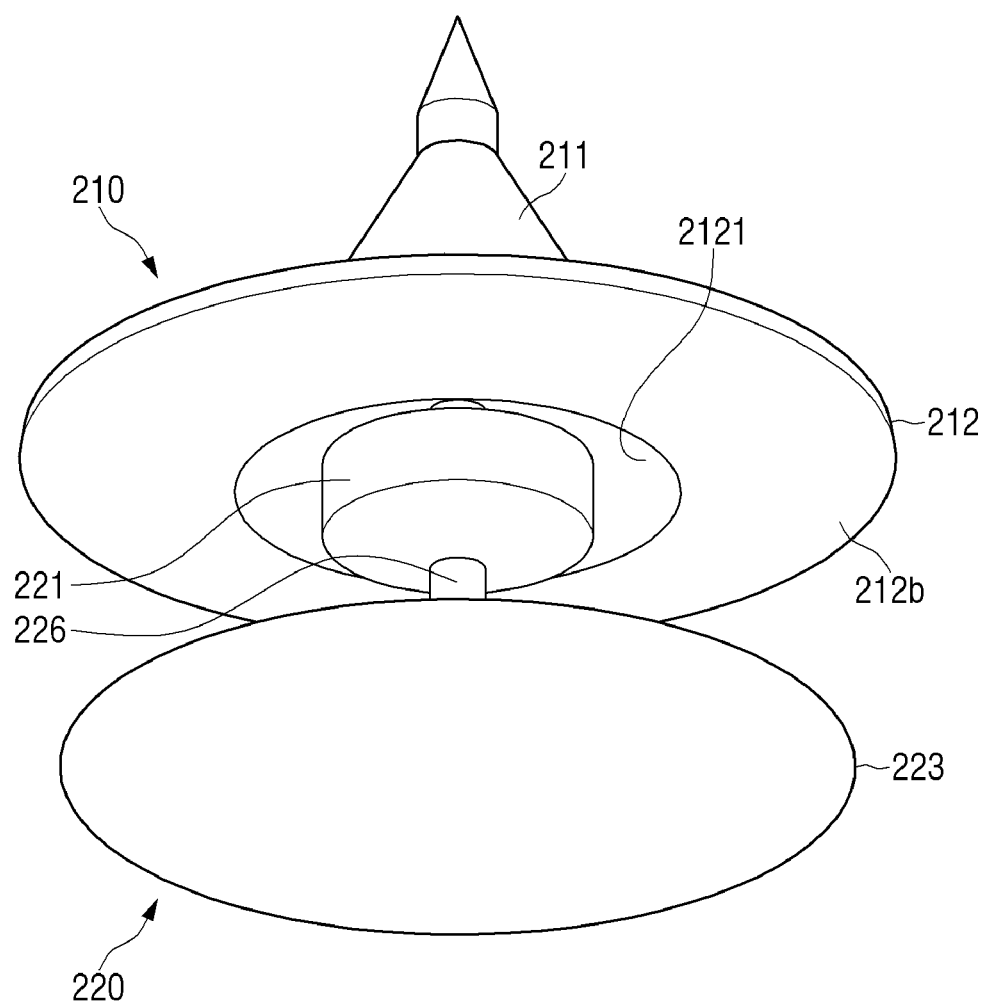
FIG. 11 is a perspective view showing a combined state of the first prevention member and the second prevention member in the apparatus for preventing backflow according to the embodiment of the present invention.
Figure 12:
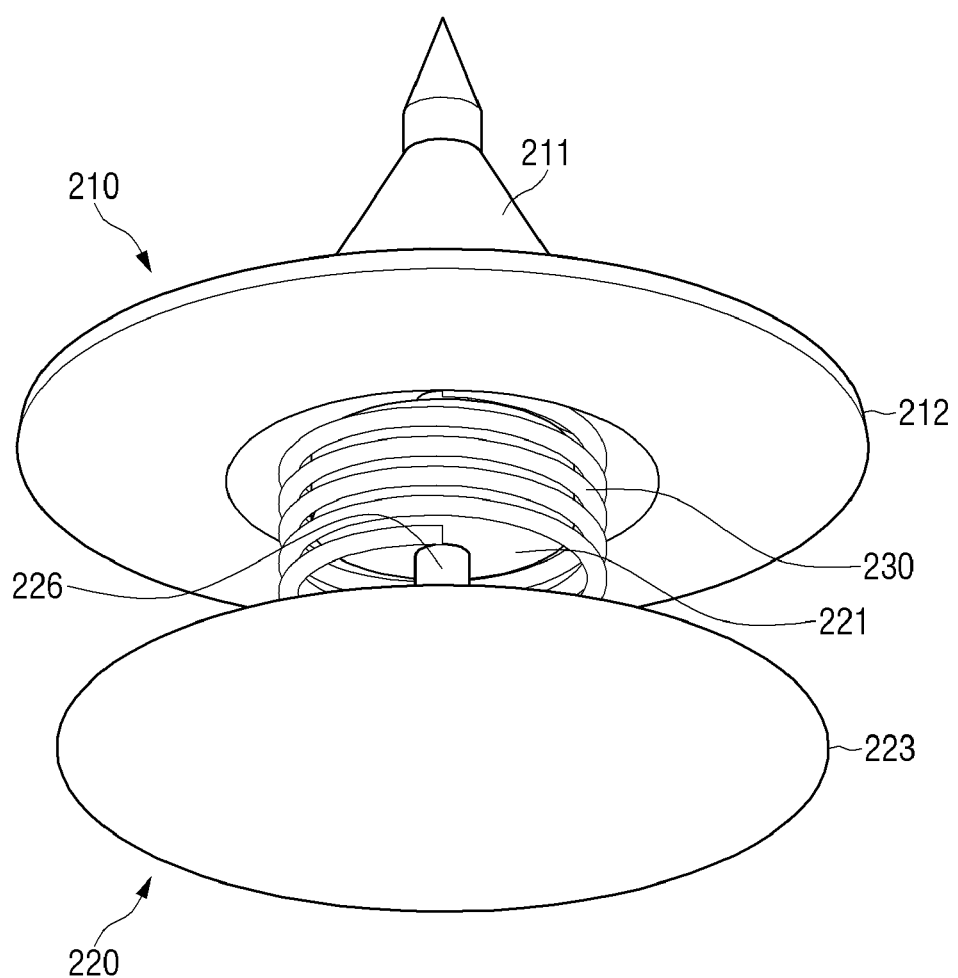
FIG. 12 is a schematic perspective view of the backflow prevention member in the apparatus for preventing backflow according to the embodiment of the present invention.

FIG. 11 is a perspective view showing a combined state of the first prevention member 210 and the second prevention member 220 in the apparatus 1 for preventing backflow according to the embodiment of the present invention. FIG. 12 is a schematic perspective view of the backflow prevention member in the apparatus 1 for preventing backflow according to the embodiment of the present invention.

Referring to FIGS. 11 and 12, the first prevention member 210 and the second prevention member 220 according to the embodiment of the present invention may have a structure that is coupled while being placed in the up and down direction.

In addition, the first prevention member 210 and the second prevention member 220 may be injection molded so that it has a structure in which the head 222 of the second prevention member 220 is seated and coupled to the accommodating space of the first prevention member 210.

In addition, the elastic member 230 may be disposed between the inlet surface 2121 on a circumferential surface of the second body 221 and the bottom surface of the first chamber 131 toward the inside of the projection. In other words, one end of the elastic member 230 may contact the inlet surface 2121, and the other end of the elastic member 230 may be sandwiched between the protrusions 1311 to contact the bottom surface of the first chamber 131. Accordingly, the elastic member 230 may provide an elastic force between the inlet surface 2121 and the bottom surface of the first chamber 131. Here, the elastic member 230 may provide an elastic force that is pushed upward to the first prevention member 210.

Figure 13A:
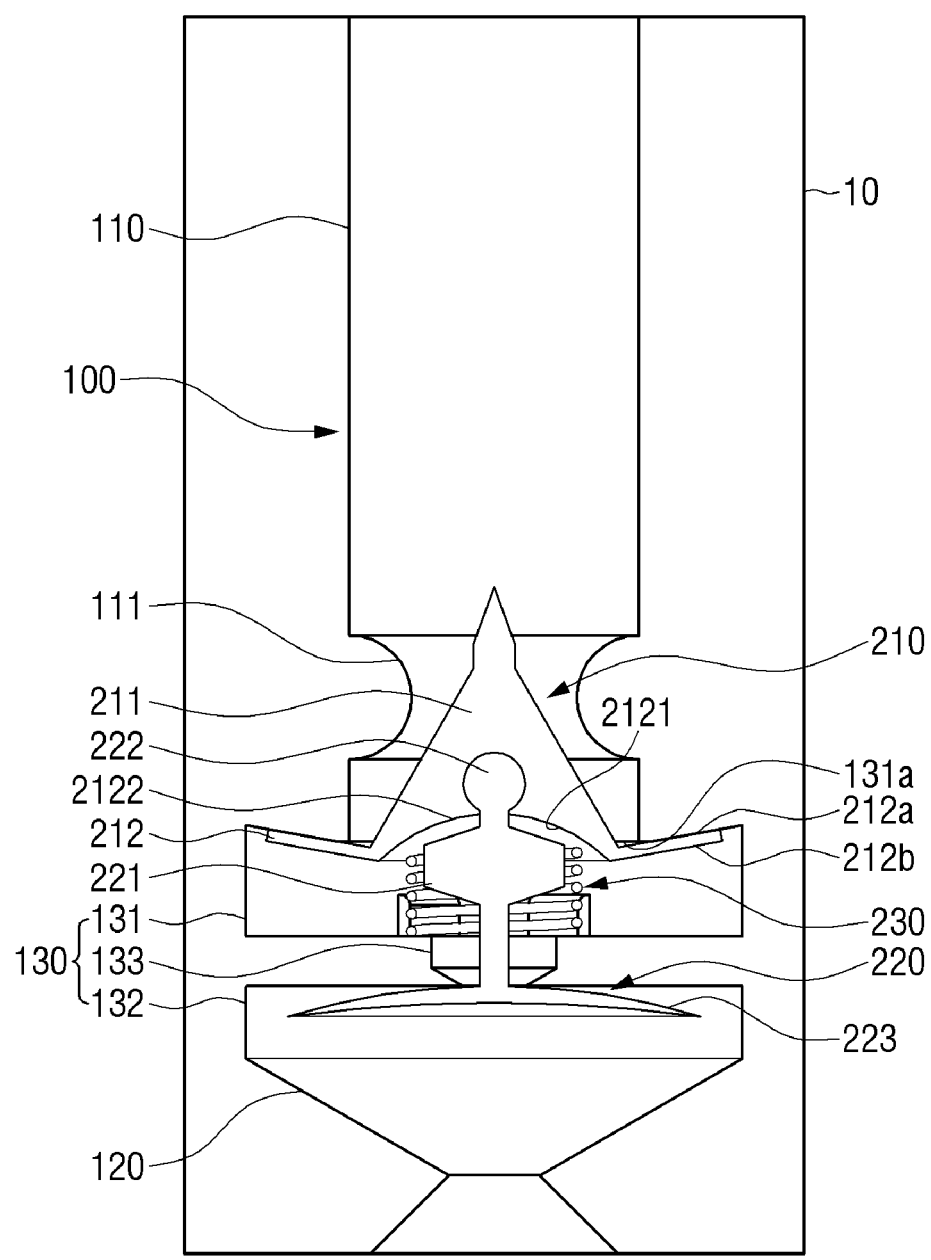
FIG. 13A is a view schematically showing a closed-closed state in the apparatus for preventing backflow according to the embodiment of the present invention.
Figure 13B:
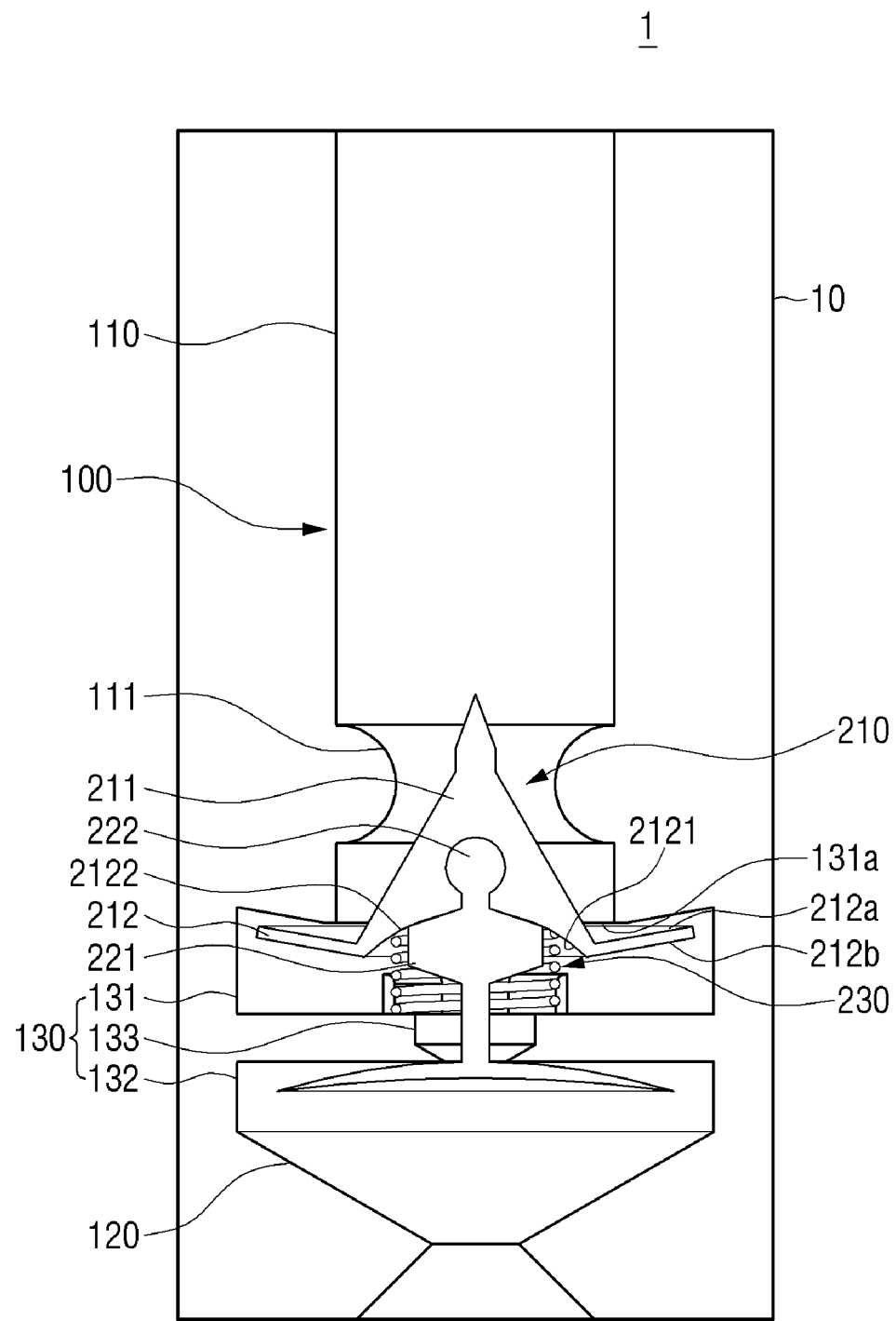
FIG. 13B is a view schematically showing a closed-open state in the apparatus for preventing backflow according to the embodiment of the present invention.
Figure 13C:
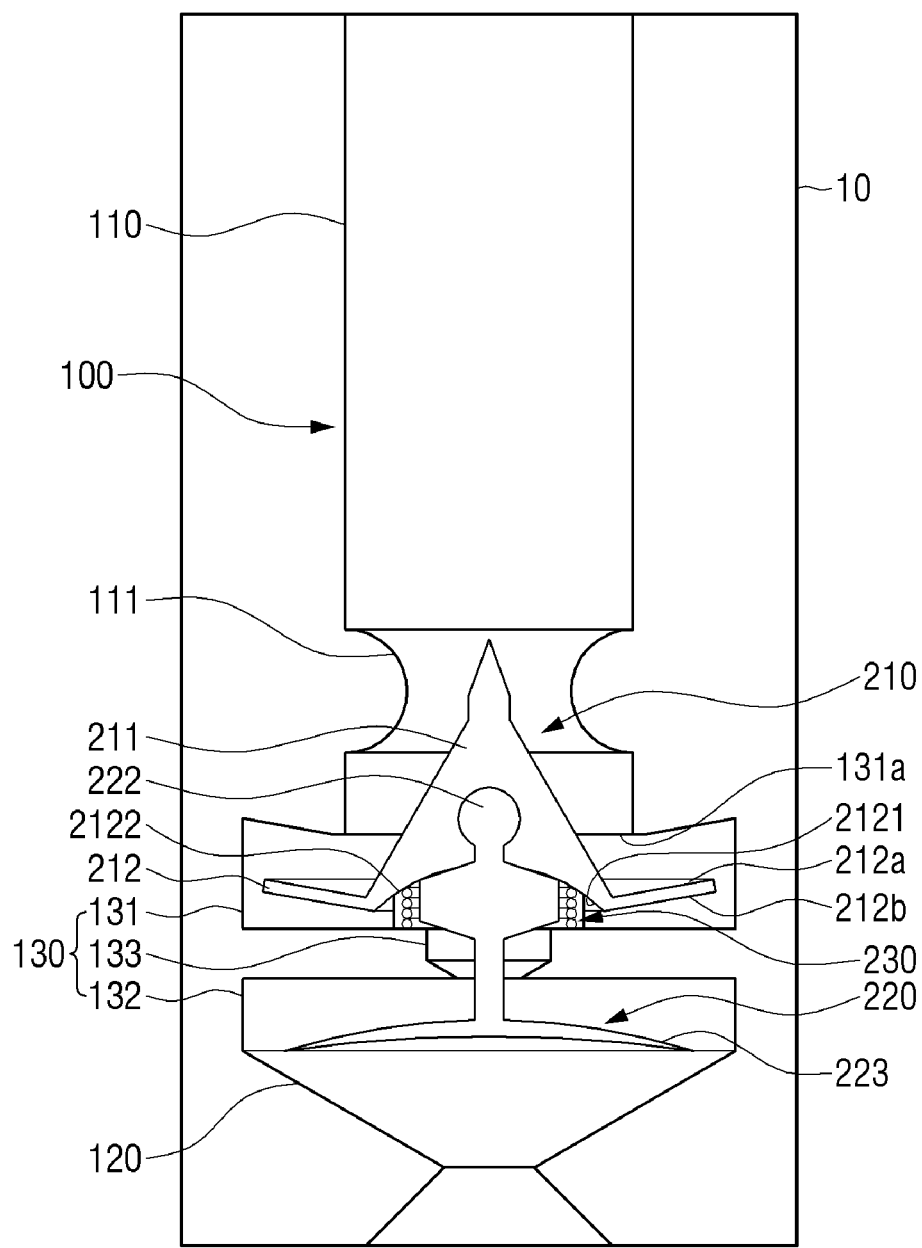
FIG. 13C is a view schematically showing an open-open state in the apparatus for preventing backflow according to the embodiment of the present invention.

FIG. 13A is a view schematically showing a closed-closed state in the apparatus 1 for preventing backflow according to the embodiment of the present invention. FIG. 13B is a view schematically showing a closed-open state in the apparatus 1 for preventing backflow according to the embodiment of the present invention. FIG. 13C is a view schematically showing an open-open state in the apparatus 1 for preventing backflow according to the embodiment of the present invention.

Referring to FIGS. 13A to 13C, the apparatus 1 for preventing backflow according to the embodiment of the present invention may implement a stepwise opening or a stepwise closing driving through a first mode driving and a second mode driving.

Specifically, when the fluid is moved forward from the top of the body 10 to the bottom, in the first mode driving, it is opened stepwise to form the flow path through the movement of the double backflow prevention member 200.

Specifically, the first mode driving is a mode in which the first opening 131a and the second opening 132a are driven to be opened and closed stepwise to be closed-closed, open-closed, and open-opened through the movement of the double backflow prevention member 200 when the fluid flows.

First, the closed-closed state of the first opening 131a and the second opening 132a may be described. When there is no flow of the fluid or the pressure is weak, the first prevention member 210 may be positioned at the top of positions that can be mounted in the first chamber 131, and the second prevention member may be positioned on the uppermost side among positions that can be mounted in the second chamber 132. In other words, by a support force of the elastic member 230, the pressing member 212 receives the elastic force to the upper side, and the pressing inclined surface 212a is in close contact with the inner inclined surface 131c to close the first opening 131a. In addition, the head 222 may be fixed by being caught inside the coupling hole 2122 inside the accommodating space. Accordingly, the sealing portion 223 is in close contact with an upper side of the second chamber 132, and closes the second opening 132a.

In a state in which the first opening member 131a and the second opening member 132a are closed-closed by the first prevention member 210 and the second prevention member 220 mounted in the above position, the first opening 131a and the second opening 132a may be implemented in the open-closed state while the first prevention member 210 is lowered, and the second prevention member 220 maintains a mounting position.

For example, the fluid may flow into the accommodating portion 100, specifically, the inflow chamber 110. After the fluid flows into, the pressure of the fluid increases between the guide protrusion 217 and the flow rate portion 111 to the lower portion of the inflow chamber 110. As a result, the pressing member 212 disposed on the upper surface of the first chamber 131 is pressed.

The pressing member 212 supported by the elastic member 230 is lowered by the pressure of the fluid. Here, the pressing member 212 is lowered so that the inlet surface 2121 is moved before it comes into contact with the second prevention member 220, specifically, the upper convex surface 221a of the one surface of the second body 221.

Due to this, the pressing inclined surface 212a in close contact with the inner inclined surface 131c of the first chamber 131 moves away from the inner inclined surface 131c, and the first opening 131a may be opened. However, as the second prevention member 220 maintains a closed mounting position, the sealing portion 223 maintains the second opening 132a in a closed state.

In the position, in a state in which the first opening 131a and the second opening 132a are open-closed by lowering the first prevention member 210 a predetermined amount and maintaining the mounting position of the second prevention member 220, the first opening 131a and the second opening 132a may be implemented in the open-open state by lowering the first prevention member 210 and also lowering the second prevention member 220.

For example, as the pressing member 212 opens the first opening 131a by pressure generated by the inflow of the fluid in a state where the fluid flows into the inflow chamber 110 and pressure according to the flow rate generated by the flow rate portion 111 and the guide protrusion 217, the fluid may flow into the first chamber 131. As the fluid flows into the first chamber 131, pressure is generated in the first chamber 131, and the pressing member 212 is lowered against the elastic force of the elastic member 230. Here, the head 222 of the second prevention member 220 is away from the coupling hole 2122. The upper convex surface 221a of the second body 221 is in contact with the inlet surface 2121, and in this state, the second prevention member 220 is pressed according to the lowering of the pressing member 212. As a result, the upper convex surface 221a of the second body 221 is lowered together until the lower convex surface 221b contacts a bottom surface of the first chamber 131. Due to this, the pressing member 212 is lowered more than the state in which the first opening 131a is opened in the open-close step. In addition, the sealing portion 223 is further away from the second opening 132a to open the second opening 132a.

As described above, the first mode driving may allow the fluid to flow into the discharge chamber 120 while the closed-closed, open-closed, and open-open are implemented step by step as described above.

When the pressure applied from the discharge chamber 120 to the inflow chamber 110 side is greater than the pressure from which the fluid moves from the inflow chamber 110 to the discharge chamber 120 due to a change in pressure, etc., i.e., when the blood is moved in the reverse direction from the bottom of the body 10 to the top, the second mode driving stepwise closes it through the movement of the double backflow prevention member 200 to block the flow path.

Specifically, the second mode driving is a mode in which the first opening 131a and the second opening 132a are driven to be opened and closed stepwise such that they are open-open, open-closed, and closed-closed through the movement of the double backflow prevention member 200 during the backflow of the fluid.

Specifically, in a state in which the first opening 131a and the second opening 132a are open-open and the fluid flows from the inflow chamber 110 to the discharge chamber 120, the first opening 131a and the second opening 132a may be implemented in the open-closed state when the pressure is increased in the reverse direction.

For example, when the pressure from the discharge chamber 120 to the inflow chamber 110 increases than the pressure that the fluid flows from the inflow chamber 110 to the discharge chamber 120, the fluid or blood flows from the discharge chamber 120 toward the inflow chamber 110. As a result, the pressure is applied to the sealing portion 223 of the second prevention member 220 in the reverse direction while the fluid or blood flows in the reverse direction, and the sealing portion 223 is pushed upward in the upward direction and is raised.

When the second prevention member 220 is raised, the second opening 132a is closed while being blocked by the sealing portion 223. Therefore, the fluid or blood flowing from the discharge chamber 120 into the second chamber 132 may no longer flow into the first chamber 131.

However, almost instantaneously, in the open-close step of the first opening 131a and the second opening 132a, i.e., in the step of closing the second opening 132a, some of them may flow backward and flow into the first chamber 131.

However, the second prevention member 220 is pushed upward in a state that the upper convex surface 221a of the second body 221 is in contact with the inlet surface 2121 due to the continuous generation of the pressure of the backwardly flowed fluid or blood, and in addition, there is the flow rate of the fluid flowing in the direction of the first opening 131a of the first chamber 131 and the elastic force of the elastic member 230. Therefore, the first opening 131a may be closed while a pressing contact surface of the pressing member 212 is in close contact with the inner contact surface.

In other words, in the open-closed step of the first opening 131a and the second opening 132a, even if the fluid or blood flows from the second chamber 132 to the first chamber 131 while the closed-closed step occurs almost simultaneously, inflow from the first chamber 131 to the inflow chamber 110 may be blocked.

Therefore, even if a condition in which the fluid or blood flows backward from the discharge chamber 120 to the inflow chamber 110 occurs, the backflow can be prevented by implementing a double closing structure and stepwise closing by the double backflow prevention chamber 130 and the double backflow prevention member 200.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

What is claimed is:

1. An apparatus for preventing backflow, comprising:
a body forming an accommodating portion which forms a transport passage of a fluid
inward, wherein the accommodating portion comprises a double backflow prevention chamber to prevent backflow of the fluid; and
a double backflow prevention member provided in the accommodating portion and stepwise implementing opening and closing of the double backflow prevention chamber,
wherein the accommodating portion comprises:
an inflow chamber provided at an upper portion of the body and into which the fluid flows;
a discharge chamber provided at a lower portion of the body, through which the fluid is discharged
the double backflow prevention member respectively provided at the lower portion of the inflow chamber and the upper portion of the discharge chamber, the double backflow prevention chamber comprising a first chamber provided below the inflow chamber and a second chamber provided above the discharge chamber and connected to the first chamber, and wherein the double backflow prevention member comprises:
- a first prevention member provided between the inflow chamber and the first chamber to open and close between the inflow chamber and the first chamber;
- a second prevention member coupled to the first prevention member and provided between the first chamber and the second chamber to open and close between the first chamber and the second chamber; and
- an elastic member provided between the second prevention member and a bottom surface of the first chamber to elastically support and move the first prevention member and the second prevention member, wherein a first opening connected to the inflow chamber and opened or closed through the double backflow prevention member is formed in an upper portion of the first chamber, wherein a second opening connected to the first chamber and opened or closed through the double backflow prevention member is formed in an upper portion of the second chamber, wherein a third opening connected to the second opening is formed in a lower portion of the first chamber, and wherein a connection flow path connecting the third opening and the second opening is formed between the first chamber and the second chamber.

2. The apparatus of claim 1, wherein the first prevention member is provided to open and close the first opening by moving an up and down direction by an inflow pressure of the fluid between the inflow chamber and the first chamber, and wherein the second prevention member is provided to open and close the second opening according to an upward and downward movement of the first prevention member between the first chamber and the second chamber.

3. The apparatus of claim 2, wherein the first prevention member comprises:
- a first body formed in a conical shape and forming an accommodating space accommodated in one end of the second prevention member inward; and
- a pressing member protruding in a lateral direction in a circumference of a lower surface of the body, the pressing member engaging with an upper surface of the first chamber and opening and closing the first opening as it moves.

4. The apparatus of claim 3, wherein a guide protrusion for guiding a flow of the fluid in a conical shape is further formed on an upper portion of the first body to be stepped with the first body.

5. The apparatus of claim 3, wherein a flow rate portion that is recessed inward to accelerate a flow rate of the fluid is formed on a circumferential surface of the inflow chamber in which the first body is positioned.

6. The apparatus of claim 3, wherein the upper surface of the first chamber forms an inner inclined surface lowering toward a direction of the first opening, and one surface of the pressing member forms a pressing inclined surface corresponding to the inner inclined surface, thereby causing the pressing inclined surface to face the inner inclined surface to close the first opening.

7. The apparatus of claim 6, wherein an inlet surface is formed on the other surface of the pressing member to flow inwardly corresponding to the one surface of the second prevention member.

8. The apparatus of claim 7, wherein a coupling hole in which one end of the second prevention member is inserted into the accommodating space and is movably formed is formed in the inlet surface.

9. The apparatus of claim 8, wherein the second prevention member comprises:
- a second body provided between the bottom surface of the first chamber and the inlet surface;
- a head provided to be connected to the upper portion of the first body through a first connecting protrusion, the head being accommodated in the accommodating space and coupled so as to prevent from being separated from the first body; and
- a sealing portion provided to be connected to a lower portion of the second body through a second connecting protrusion and disposed inside the second chamber, the sealing portion opening or closing the second opening according to a raising and lowering movement of the second prevention member.

10. The apparatus of claim 9, wherein one surface and the other surface of the second body form convex surfaces convex in the up and down direction, respectively, with respect to the first connecting protrusion and the second connecting protrusion.

11. The apparatus of claim 10, wherein the convex surface of the one surface of the second body is in contact with or released from the inlet surface according to a raising and lowering movement of the first prevention member.

12. The apparatus of claim 11, wherein a protrusion protruding upward is provided around a periphery of the third opening in the bottom surface of the first chamber, and the elastic member is disposed between the inlet surface in a circumferential surface of the second body and the bottom surface of the first chamber toward an inside of the projection, thereby providing an elastic force to the first prevention member.

13. The apparatus of claim 12, wherein the sealing portion is formed in a convex dish shape.

* * * * *